United States Patent [19]

Manis et al.

[11] 4,332,900
[45] Jun. 1, 1982

[54] CONSTRUCTION OF CO-INTEGRATE PLASMIDS FROM PLASMIDS OF STREPTOMYCES AND ESCHERICHIA

[75] Inventors: Jack J. Manis, Portage; Sarah K. Highlander, Oshtemo Township, Kalamazoo County, both of Mich.

[73] Assignee: The Upjohn Company, Kalamazoo, Mich.

[21] Appl. No.: 192,727

[22] Filed: Oct. 1, 1980

[51] Int. Cl.³ .................... C12N 15/00; C12N 1/20; C12N 1/00; C12P 19/34
[52] U.S. Cl. .................................. 435/172; 435/91; 435/253; 435/317; 435/820; 435/849
[58] Field of Search .................. 435/172, 253, 68, 317

[56] References Cited

U.S. PATENT DOCUMENTS 4,237,224 12/1980 Cohen et al. .......................... 435/68
4,273,875 6/1981 Manis .................................. 435/253

OTHER PUBLICATIONS

Muray et al. in *Recombinant DNA and Gentic Experimentation*.
Morgan et al., (ed.) Pergamon Press, (1979), pp. 53–64.
Blattner et al., Science 196, 161, (1977).
Armstrong et al., Science 196, 172, (1977).
Bolivar, Gene 4, 121, (1978).

*Primary Examiner*—Alvin E. Tanenholtz
*Assistant Examiner*—James Martinell
*Attorney, Agent, or Firm*—Roman Saliwanchik

[57] ABSTRACT

Novel chemical compounds, recombinant plasmids pUC1019 and pUC-1020, which are obtained by covalent linkage of ca. 4.2 kb BclI restriction endonuclease fragment of the *Streptomyces espinosus* plasmid pUC6 into the BamHI endonuclease site of the E. coli plasmid pBR322. Plasmid pUC1024 is obtained by restructuring plasmid pUC1019. These plasmids are useful as cloning vehicles in recombinant DNA work. For example, using DNA methodology, a desired gene, for example, the insulin gene, can be inserted into the plasmids and the resulting plasmids can then be transformed into a suitable host microbe which, upon culturing, produces the desired insulin.

14 Claims, 5 Drawing Figures

CONSTRUCTION OF CO-INTEGRATE PLASMIDS FROM PLASMIDS OF STREPTOMYCES AND ESCHERICHIA

BACKGROUND OF THE INVENTION

The development of plasmid vectors useful for recombinant DNA genetics among microorganisms is well known. The editorial in Science, Vol. 196, April, 1977, gives a good summary of DNA research. This editorial is accompanied by a number of supporting papers in the same issue of Science.

Similar DNA work is currently being done on industrially important microorganisms of the genus Streptomyces. [Bibb, M. J., Ward, J. M., and Hopwood, D. A. 1978. "Transformation of plasmid DNA into Streptomyces at high frequency." Nature 274, 398-400.] Though plasmid DNA's have been detected in several streptomycetes [Huber, M. L. B. and Godfrey, O. 1978. "A general method for lysis of Streptomyces species." Can. J. Microbiol. 24, 631-632.] [Schrempf, H., Bujard, H., Hopwood, D. A. and Goebel, W. 1975. "Isolation of covalently closed circular deoxyribonucleic acid from *Streptomyces coelicolor* A3(2)." J. Bacteriol. 121, 416-421.] [Umezawa, H. 1977. "Microbial secondary metabolites with potential use in cancer treatment (Plasmid involvement in biosynthesis and compounds)." Biomedicine 26, 236-249.], [Malik, V. S. 1977. Preparative Method for the isolation of super-coiled DNA from a chloramphenicol producing streptomycete. J. Antibiotics 30, 897899], only a few streptomycete plasmids have been physically isolated and extensively characterized [Schrempf, supra]. See also [Bibb, M., Schottel, J. L., and Cohen, S. N. 1980. A DNA cloning system for interspecies gene transfer in antibiotic-producing Streptomyces. Nature 284, 526-531.] and [Thompson, C. J., Ward, J. M. and Hopwood, D. A. 1980. DNA cloning in Streptomyces:resistance genes from antibiotic-producing species. Nature 286, 525-529.] The existence of other plasmids in the genus Streptomyces has been inferred from reported genetic data as follows:

(1) Akagawa, H., Okanishi, M. and Umezawa, H. 1975. "A plasmid involved in chloramphenicol production in *Streptomyces venezuelae*: Evidence from genetic mapping." J. Gen. Microbiol. 90, 336-346.

(2) Freeman, R. F. and Hopwood, D. A. 1978. "Unstable naturally occurring resistance to antibiotics in Streptomyces." J. Gen. Microbiol. 106, 377-381.

(3) Friend, E. J., Warren, M. and Hopwood, D. A. 1978. "Genetic evidence for a plasmid controlling fertility in an industrial strain of *Streptomyces rimosus*." J. Gen. Microbiol. 106, 201-206.

(4) Hopwood, D. A. and Wright, H. M. 1973. "A plasmid of *Streptomyces coelicolor* carrying a chromosomal locus and its inter-specific transfer." J. Gen. Microbiol. 79, 331-342.

(5) Hotta, K., Okami, Y. and Umezawa, H. 1977. "Elimination of the ability of a kanamycin-producing strain to biosynthesize deoxystreptamine moiety by acriflavine." J. Antibiotics 30, 1146-1149.

(6) Kirby, R., Wright, L. F. and Hopwood, D. A. 1975. "Plasmid-determined antibiotic synthesis and resistance in *Streptomyces coelicolor*." Nature 254, 265-267.

(7) Kirby, R. and Hopwood, D. A. 1977. "Genetic determination of methylenomycin synthesis by the SCPI plasmid of *Streptomyces coelicolor* A3(2)." J. Gen. Microbiol. 98, 239-252.

(8) Okanishi, M., Ohta, T. and Umezawa, H. 1969. "Possible control of formation of aerial mycelium and antibiotic production in Streptomyces by episomic factors." J. Antibiotics 33, 45-47.

Plasmid pUC6 was isolated from *Streptomyces espinosus* biotype 23724a, NRRL 11439.

Plasmid pBR322 is a well known plasmid which can be obtained from *E. coli* RR1, NRRL B-12014. The restriction endonuclease map for pBR322 is published; Sutcliff, J. G. "pBR322 restricting map derived from the DNA sequence: accurate DNA size markers up to 4361 nucleotide pairs long." Nucleic Acids Research 5, 2721-2728, 1978. This map is incorporated herein by reference to the above publication.

BRIEF SUMMARY OF THE INVENTION

Plasmids pUC1019 and pUC1020 are obtained by the in vitro linkage of ~4.2 kb BclI restriction endonuclease fragment of the *S. espinosus* plasmid pUC6 into the BamH1 endonuclease site of the *E. coli* plasmid pBR322.

Plasmids pUC1019 and pUC1020 constitute the insertion of this BclI fragment in the two possible orientations in pBR322. In a like manner, the 4.1 and 0.9 kb BclI restriction fragments of pUC6 can be recombined with pBR322.

The invention further includes the construction of plasmid pUC-1024, which is derived from pUC1019 by in vitro deletion of DNA sequences between endonuclease PvuII sites. Plasmid pUC1024 is ~3.5 kilobases (kb) smaller than pUC1019.

The plasmids, advantageously, are transformed into a suitable host, for example, *E. coli*.

Plasmids pUC1019 and pUC1020 are recombinant DNA molecules consisting of the entire genome of the small (~2.6×10$^6$ dalton) high copy number (~30/chromosome) *E. coli* plasmid pBR322 and ~46% (4.2 kb) of the genome of the small (~6.0×10$^6$ daltons) high copy number (~30/chromosome) *S. espinosus* plasmid pUC6. Plasmids pUC1019 and pUC1020 contain single sites for the restriction endonucleases EcoRI, PstI, HindIII and XhoI. The XhoI site will also allow the cloning of SalI restriction fragments. Hence plasmids pUC1019 and pUC1020 represent DNA molecules which may function as vectors in both *E. coli* and Streptomyces and represent valuable intermediates for the development of better host-vector systems.

Plasmids pUC1019, pUC1020, and pUC1024 are characterized by the restriction maps shown in FIGS. 2, 3, and 5, respectively, of the drawings. The restriction endonuclease abbreviations shown in the drawings are standard and well known in the art.

Plasmid pUC6 is obtainable from the novel microorganism *Streptomyces espinosus* biotype 23724a, NRRL 11439. This plasmid can be obtained from NRRL 11439 by growing the culture on a suitable medium, fragmenting the mycelia, incubating the fragmented mycelia, harvesting the culture after a suitable time, and then lysing the mycelia. From this lysate it is possible to isolate essentially pure pUC6. pUC6 is characterized by standard characterization tests which include its molecular weight, approximately 6.0 megadaltons, sensitivity to restriction endonucleases, infra, and presence at 20-40 copies per *S. espinosus* NRRL 11439 cell.

REFERENCE TO THE DRAWINGS

FIG. 1—This shows the isolation scheme of the plasmids.

FIG. 2—Restriction endonuclease cleavage map for pUC1019.

FIG. 3—Restriction endonuclease cleavage mpa for pUC1020.

FIG. 4—Construction of recombinant plasmid pUC1024.

FIG. 5—Restriction endonuclease cleavage map for pUC1024.

The maps are constructed on the basis of plasmids pUC1019 and pUC1020 having a molecular weight of ca. 5.7 megadaltons or a molecular length of ca. 8.6 kilobases (kb). Plasmid pUC1024 has a molecular length of ca. 5.1 kb. It retains the locus conferring genetic instability to plasmid pUC1019 in E. coli hosts. Plasmid pUC1024 has single restriction sites for the endonucleases EcoRI, HindIII, PstI and PvuII. The PvuII site will allow the cloning of blunt ended DNA fragments from a wide range of restriction enzyme digests or from other properly prepared DNA fragments. The restriction endonuclease abbreviations are as follows: (1) BglII is an enzyme from *Bacillus globigii;* (2) BclI is an enzyme from *Bacillus caldolyticus;* (3) PvuII is an enzyme from *Proteus vulgaris;* and (4) XhoI is an enzyme from *Xanthomonas holicola.* pUC1019, pUC1020, and pUC1024, can be used to create recombinant plasmids which can be introduced into host microbes by transformation. The process of creating recombinant plasmids is well known in the art. Such a process comprises cleaving the isolated vector plasmid at a specific site(s) by means of a restriction endonuclease, for example, BglII, XhoI, and the like. The plasmid, which is a circular DNA molecule, is thus converted into a linear DNA molecule by the enzyme which cuts the two DNA strands at a specific site. Other non-vector DNA is similarly cleaved with the same enzyme. Upon mixing the linear vector or portions thereof and non-vector DNA's, their single-stranded or blunt ends can pair with each other and in the presence of a second enzyme known as polynucleotide ligase can be covalently joined to form a single circle of DNA.

The above procedure also can be used to insert a length of DNA from a higher animal into pUC1019, pUC1020, or pUC1024. For example, the DNA which codes for ribosomal RNA in the frog can be recombined with pUC1019 DNA. The resulting circular DNA molecules consist of plasmid pUC1019 with an inserted length of frog rDNA.

The recombinant plasmids containing a desired genetic element, prepared by using pUC1019, pUC1020, or pUC1024, can be introduced into a host organism for expression. Examples of valuable genes which can be inserted into host organisms by the above described process are genes coding for somatostatin, rat proinsulin, interferon, and proteases.

The usefulness of plasmids pUC1019, pUC1020, and pUC1024 is derived from their capacity to function as plasmid vectors in industrially important microorganisms, e.g., Streptomyces. Also, pUC1019, pUC1020, and pUC1024 are especially useful because of their single restriction sites. Hence, cloning of genetic information from Streptomyces into pUC1019, pUC1020, or pUC1024 provides a means of increasing the production of commercially important products from these organisms, e.g., antibiotics.

This approach is compared to the concept of cloning genes for antibiotic production into the well characterized *Escherichia coli* K-12 host-vector system. The *E. coli* system has the disadvantage that it has been found that genes from some Gram-positive organisms, e.g., Bacillus, do not express well in the Gram-negative *E. coli* host. Likewise, plasmids from Gram-negative organisms are not maintained in Gram-positive hosts, and Gram-negative genetic information is either expressed poorly or not at all in Gram-positive hosts. This clearly argues for the advantage of a Gram-positive host-vector system and argues the usefulness of plasmid pUC1019, pUC1020, or pUC1024, in such a system.

In general, the use of a host-vector system to produce a product foreign to that host requires the introduction of the genes for the entire biosynthetic pathway of the product to the new host. As discussed above, this may lead to problems of genetic expression, but may also generate new and/or increased problems in the fermentation of the microorganisms and in the extraction and purification of the product. A perhaps more useful approach is to introduce a plasmid vector into a host which normally produces the product and clone onto that plasmid the genes for biosynthesis of the product. At the very least, problems of fermentation and product extraction and purification should be minimized. Additionally, in this cloning system it may not be necessary to clone and amplify all the genes of the biosynthetic pathway, but rather it may be necessary only to clone regulatory genes or genes coding for the enzymes that are rate limiting in product biosynthesis. Since pUC1019 and pUC1020 are cointegrate plasmids, they can be used to clone DNA sequences in *E. coli* or within the genera of Streptomyces and Micromonospora, as well as within other microbes.

DETAILED DESCRIPTION OF THE INVENTION

The Microorganisms and Plasmids

Figure 1:
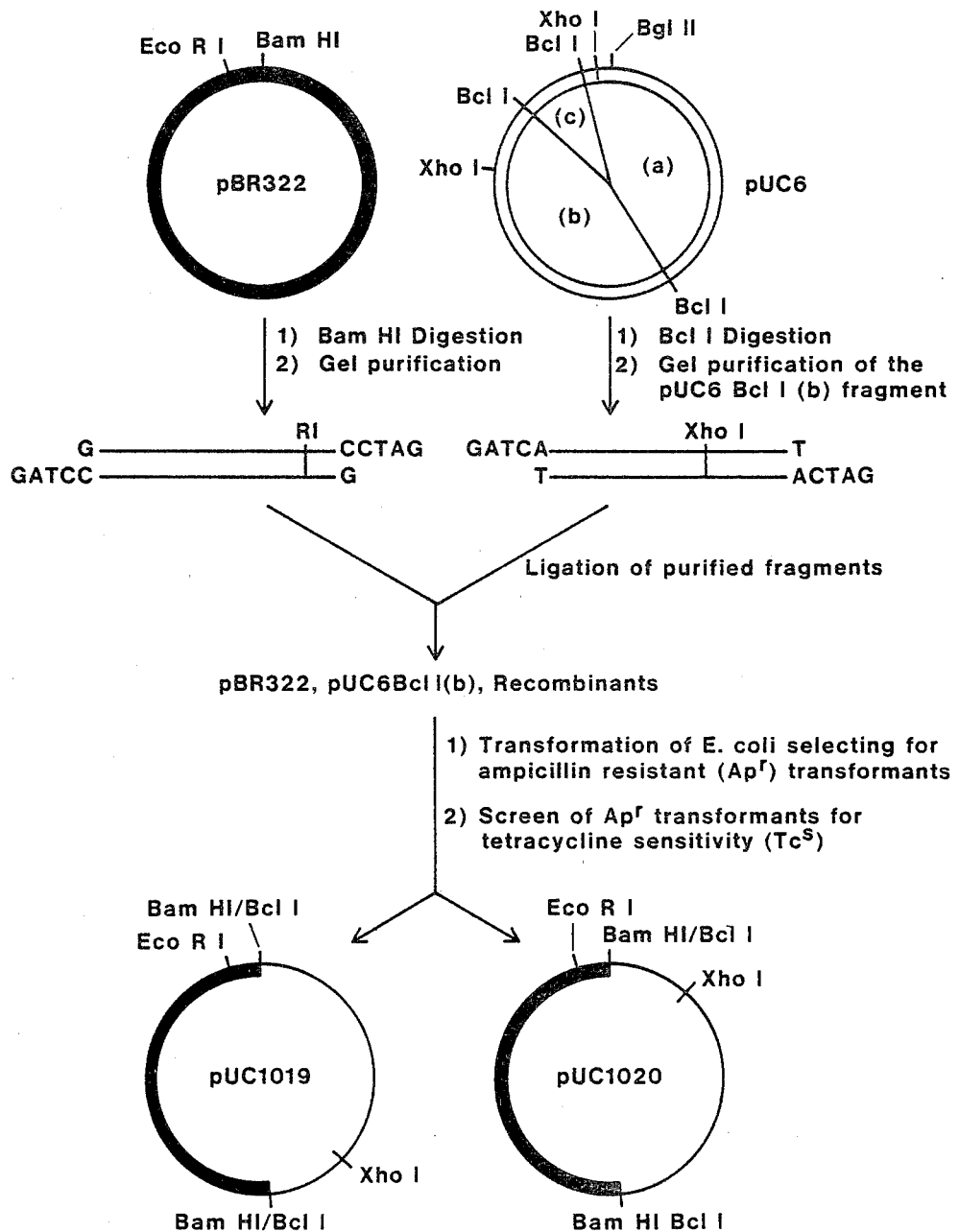

The following microorganisms are available from the permanent collection of the Northern Regional Research Laboratory, U.S. Department of Agriculture, Peoria, Ill., U.S.A.

NRRL B-12110—*E. coli* CSH50
NRRL B-11439—*S. espinosus* biotype 23724a
NRRL B-12014—*E. coli* RR1 (pBR322)
NRRL B-12252—*E. coli* CSH50 (pUC1019)
NRRL B-12253—*E. coli* CSH50 (pUC1020)
NRRL B-12254—*E. coli* RR1 (pUC1024)
NRRL B-12186—*E. coli* RR1

These deposits are available to the public upon the grant of a patent to the assignee, The Upjohn Company, disclosing them. The deposits are also available as required by foreign patent laws in countries wherein counterparts of the subject application, or its progeny, are filed. However, it should be understood that the availability of a deposit does not constitute a license to practice the subject invention in derogation of patent rights granted by governmental action.

The following examples are illustrative of the process and products of the subject invention but are not to be construed as limiting. All percentages are by weight and all solvent mixture proportions are by volume unless otherwise noted.

EXAMPLE 1

Isolation of Vector pBR322 DNA from *E. coli* NRRL B-12014

A 100 ml. culture of *E. coli* RR1 (pBR322) is grown overnight in L-broth which consists of the following ingredients:

| | |
|---|---|
| Bacto tryptone (Difco) | 10 g./liter |
| Bacto yeast extract (Difco) | 5 g./liter |
| NaCl | 5 g./liter |
| Ampicillin | 50 mg./liter |

The cells are recovered by centrifugation at 17,000×g. for 10 minutes in a refrigerated centrifuge. The pellet is suspended in 2.5 ml. 50 mM tris buffer (pH 8) containing 25% sucrose. One-half ml. of lysozyme stock solution is added (5 mg./ml. in TES buffer). The mixture is allowed to stand in ice for 5 minutes. At this point 1 ml. EDTA (0.25 M, pH 8) is added and the mixture is again allowed to stand in ice for 5 minutes. One and a quarter ml. of 5 N NaCl and 1 ml. 10% SDS (sodium dodecyl sulfate) are then added. The mixture is shaken on a Vortex and incubated at 37° C. for 20 minutes. Then 10 μl of ribonuclease (20 mg./ml.) is added and the sample is again incubated at 37° C. for 20 minutes. The mixture is then kept in ice overnight and then centrifuged at 35,000×g. for 30 minutes in a refrigerated centrifuge. 2 ml. of the supernatant solution (lysate) are carefully removed with a pipette. Four and one-half ml. of TES buffer (30 mM tris.HCl, pH 8, 5 mM EDTA.Na$_2$, 50 mM NaCl) are mixed with 1.5 ml. EtBr (ethidium bromide) stock (1 mg./ml. in TES buffer) and 7.5 g. solid CsCl. After the salt has dissolved, 2 ml. of the lysate, described above, is added and the mixture is transferred into a polyallomer tube fitting a titanium 50 (50 Ti) head (Beckman ultracentrifuge). The tubes are filled to the top with mineral oil and centrifuged in a Beckman ultracentrifuge at 40,000 rpm in a 50 Ti head at 15° C. for at least 2 days. The DNA is located under a long wave UV-lamp and the heavier band containing the plasmid DNA is removed with a syringe by puncturing the tube wall from the side. The samples are extensively dialysed against 200 volumes of TES buffer at 4° C. Following dialysis, 1/10 sample volume of a 3 M Na acetate stock solution is added and the plasmid DNA is precipitated by the addition of 2 volumes of cold ethanol. The resulting pellet is then lyophilized and redissolved in 200 μl 10 mM tris buffer, pH 7.8 containing 1 mM EDTA.Na$_2$ and frozen for storage.

EXAMPLE 2

Isolation of Plasmid pUC6 from a Biologically Pure Culture of *Streptomyces espinosus*, biotype 23724a, NRRL 11439

The spores from a biologically pure culture of *Streptomyces espinosus* biotype 23724a, NRRL 11,439, are inoculated into 10 ml. of the following Difco Antibiotic Medium No. 3 Broth (Difco Labs., Detroit, Mich.): 0.15% Beef extract; 0.15% yeast extract; 0.5% peptone; 0.1% glucose; 0.35% NaCl; 0.368% K$_2$HPO$_4$; 0.132% KH$_2$PO$_4$.

The medium has previously been sterilized in a 50 ml. Erlenmeyer flask. After inoculation, the flask is incubated at 37° C. for about 36 to 48 hours on a Gump or New Brunswick rotary shaker operating at 100-250 rpm. Upon completion of the incubation, the mycelia-broth suspension in the flasks is homogenized under sterile conditions and is then mixed in a sterile 125 ml. Erlenmeyer flask containing 10 ml. of the above medium and also, advantageously 68% (w/v) sucrose and 1% (w/v) glycine. The addition of sucrose and glycine facilitates the subsequent lysing of the cells. The amounts of sucrose and glycine in the medium can be varied by routine adjustments with the goal being to facilitate the subsequent lysing of the cells. The flask is then incubated further for another 36 to 48 hours at 37° C. on a Gump rotary shaker, as above. After this incubation, the mycelia are separated from the broth by low speed centrifugation, for example, at 6000×g. for 15 minutes at 4° C. and decantation of the supernatant from the mycelial pellet.

The supernatant is discarded and the pellet is resuspended in 1.5 ml. of an isotonic buffer containing ethylenediaminotetraacetic acid (EDTA) and sucrose, e.g., TES buffer [0.03 M tris(hydroxymethyl)aminomethane (Tris), 0.005 M EDTA and 0.05 M NaCl; pH=8.0] containing 20% (w/v) sucrose. Next, 1.5 ml. of a 5 mg./ml. solution of lysozyme in the same buffer is added and the mixture is incubated at 37° C. for 30 minutes with occasional mixing. Then, 1.5 ml. of 0.25 M EDTA (pH=8.0) is added and this mixture is incubated 15 minutes at 37° C. Subsequently, the cell suspension is lysed by the addition of 2.5 ml. of a lytic mixture, e.g. [1.0% (w/v) Brij-58 (a detergent sold by Pierce Chem. Co., Rockford, Ill.), 0.4% (w/v) deoxycholic acid, 0.05 M Tris (pH=8.0) and 0.06 M EDTA] and incubation of this mixture at 37° C. for 20 minutes. The lysate is then sheared by passing it 5-10 times through a 10 ml. pipette. The sheared lysate is then digested with ribonuclease (140 μg/ml.) and pronase (300 μg/ml.) for an additional 20 minutes at 37° C. Alternatively, the cell-lysozyme-EDTA mixture can be digested with ribonuclease and pronase before lysis with a lytic agent such as 2% sodium dodecyl sulfate in water.

This crude lysate material is then mixed with a salt, for example, cesium chloride (preferred), and cesium sulfate, and the intercalating dye ethidium bromide to give a solution of density ρ=1.550. This solution is centrifuged to equilibrium at 145,000×g. (isopycnic density gradient centrifugation). The covalently closed circular plasmid DNA is then visible in the centrifuge tube under long wave ultraviolet (320 nm) illumination as a faint fluorescent band below the intensely fluorescent band of linear chromosomal and plasmid DNA's.

Covalently closed circular plasmid DNA is prepared for characterization by removing it from the isopycnic gradients, extracting the ethidium bromide by two treatments with one-third volume of isopropyl alcohol and then dialyzing the aqueous phase against an appropriate buffer, e.g., 0.1×SSC buffer (0.015 M NaCl, 0.0015 M sodium citrate; pH=7.4) to yield essentially pure pUC6.

Characteristics of pUC6

Molecular Weight: ca. 6.0 megadaltons
Copies per Cell: 20-40

Restriction Endonuclease Sensitivities: pUC6 has the following sensitivies to restriction endonucleases.

| Plasmid Sensitivities to Restriction Endonucleases | | | |
|---|---|---|---|
| # Cleavage Sites | | # Cleavage Sites | |
| Enzyme | pUC6 | Enzyme | pUC6 |
| BglI | >7 | BglII | 1 |
| BamHI | 0 | HpaI | 0 |
| HpaII | Many | HindIII | 0 |
| EcoRI | 0 | KpnI | 0 |
| PstI | 0 | PvuII | 4 |
| MboII | >5 | AvaI | >7 |
| XbaI | 0 | XhoI | 2 |
| SalI | 5-6 | SmaI | >5 |
| HincII | >7 | BclI | 3 |

These results were obtained by digestion of pUC6 DNA in the presence of an excess of restriction endonuclease. The number of restriction sites were determined from the number of resolvable fragments in either 0.7 or 1.0% agarose gels.

EXAMPLE 3

Preparation of Plasmids pUC1019 and pUC1020

Plasmids pUC6 and pBR322, prepared as described above, are linearized by digestion with restriction endonucleases BclI and BamHI respectively. Plasmid pBR322 DNA is digested with BamHI restriction enzyme by mixing ~50 μl. of DNA (~0.5 μg) solution in TE buffer (0.01 M Tris .HCl, 0.001 M $Na_2$ EDTA; pH 8.0) with 50 μl of 2X restriction buffer (Post et al., Cell 15, 215-229, 1978) and 4 units of BamHI enzyme preparation. This mixture is incubated at 37° C. for 1 hour. The digest is then applied to a 1% preparative low melting point agarose gel and electrophoresed for ~3 hours at 50 volts and 4° C. The resolved DNA fragments are visualized by ethidium bromide staining and long wave ultraviolet light illumination. The region of the gel containing the DNA is excised from gel and heated to 65° C. in the presence of 1.5 ml. of TE buffer to melt the gel and release the DNA from the gel matrix. This suspension is chilled and centrifuged at 37,000×g to pellet the agarose. The supernatant is decanted and saved. The agarose pellet is extracted a second time by heating to 65° C. with TE buffer. The two supernatants are pooled and ethanol precipitated by the addition of 0.1 volume of Na Acetate and 2 volumes 95% ethanol at −20° C. The DNA precipitate is collected by centrifugation at 85,000×g at 4° C. for 60 minutes. The precipitate is redissolved in 100 μl of TE buffer. This sample is used for ligation as described below.

Plasmid pUC6 is subjected to BclI digestion in a reaction mixture containing 50 μl of pUC6 DNA (~0.5 μg) solution in TE buffer and 50 μl of 2X BclI restriction buffer and 4 units of BclI enzyme. This mixture is incubated at 37° C. for one hour and the digest placed in and isolated from a preparative agarose gel electrophoresis system as described above.

For ligation, 25 μl of BamHI digested pBR322 DNA, 25 μl of BclI digested pUC6 DNA and 20 μl DD $H_2O$ are combined. Ten μl 100 mM DDT, 10 μl 50 mM $MgCl_2$ and 10 μl of 0.5 mM ATP are combined with the restricted DNA mixture. Finally, 1.0 unit of $T_4$ DNA ligase is added and the sample is kept in ice for 1-2 days.

For transformation into *E. coli* CSH50, inoculum is grown overnight in L-broth and diluted 1:100 into fresh L-broth the next day. The cells are incubated at 37° C. and allowed to grow to an $OD_{650}$ of 0.2. At this point 50 ml. of culture is centrifuged in the cold, the pellet resuspended in 20 ml. cold 100 mM $CaCl_2$, incubated at 0° C. for 20-25 minutes and centrifuged again. The pellet is then resuspended in 0.5 ml. cold 100 mM $CaCl_2$ solution and kept at 0°-4° C. for 24 hours. (Dagert, M. and Ehrlich, S. D. 1979, Gene 6: 23-28) One hundred μl of pUC1019 and pUC1020 ligase mixture (see above) is mixed with 500 μl cell suspension. This mixture is kept in ice for 10 minutes, and then at 37° C. for 5 minutes. Ten to 20 ml. of L-broth is added and the cell suspension is incubated 1-2 hours at 37° C. Next, 100 μl aliquots are plated on freshly prepared agar plates containing 25 ml. of L-broth, 1.5% agar, and 50 μg of ampicillin/ml. Colonies are selected and scored for tetracycline sensitivity.

Suspected recombinant DNA containing transformants are then grown in 25 ml. cultures. Cleared lysates are prepared by pelleting the cells from the culture medium at ~10,000×g. The pellet is resuspended in 10 ml. of cold TES buffer (30 mM Tirs.HCl, 5 mM $Na_2$ EDTA and 50 mM NaCl, pH 8.0) and pelleted again. This pellet is resuspended in 1 ml. of TES buffer containing 20% sucrose. 0.2 ml. of lysozyme solution (5 mg./ml. in TES) is added and incubated on ice 15 minutes at which time 0.4 ml. of 0.25 M $Na_2$ EDTA (pH 8.0) is added and the incubation continued 15 minutes. 1.6 ml. of a lytic mix (1% Brij 58, 0.4% Na deoxycholate, 0.05 M Tris.HCl, 62.5 mM $Na_2$ EDTA; pH 8.0) is added and the lysate incubated an additional 15 minutes at 4° C. The lysate is sheared by passage 5 times through a 10 ml. pipette. The bulk of the cellular DNA and debris are removed by centrifugation at 48,000×g for 30 minutes. The cleared lysate is digested successively for 15-minute intervals with pancreatic RNAse A (100 mcg./ml.) and Pronase (200 mcg./ml.) at 37° C. These lysate are then centrifuged in a CsCl-ethidium bromide isopycnic density gradient. Plasmid DNA isolated from these gradients is characterized by digestion with restriction endonuclease.

EXAMPLE 4

Preparation of Plasmid pUC1024

Plasmid pUC1019, prepared as described in Example 3, is linearized by digestion with restriction endonuclease PvuII as follows:

Approximately 0.5 μg of pUC1019 DNA in 25 μl of TE buffer is mixed with an equal volume of 2X PvuII restriction enzyme buffer (0.3 M NaCl, 12 mM Tris.HCl [pH 7.4], 12 mM $MgCl_2$, 12 mM 2-mercaptoethanol) and two units of PvuII restriction enzyme. This sample is digested for one hour at 37° C.

The resulting digest is then applied to a 1% preparative low melting point agarose gel and electrophoresed for ~3 hours at 50 volts and 4° C. The remainder of the agarose gel procedure is as described above in Example 3. The appropriate PvuII fragment is isolated and ligated, as described above in Example 3.

Transformation of the ligated plasmid, which is now plasmid pUC1024, into *E. coli* RR1 is as described in Example 3.

Recombinant plasmids were characterized by cleavage with restriction endonucleases.

Restriction endonucleases were obtained as commercial preparations from Miles Laboratoris, Bethesda Research Laboratories, and New England Biolabs. Enzyme diges-tions were prepared in accordance with the conditions specified by the suppliers using at least a two-fold excess of endonuclease.

The digested samples were applied to 0.7–1% agarose gels and were electrophoresed for 2 hours at a constant applied voltage of 10–15 v/cm of gel height. [Sharp, P. A., Sugden, J. and Sambrook, J. 1973. Detection of two restriction endonuclease activities in *Haemophilus parainfluenzae* using analytical agarose-ethidium bromide electrophoresis. Biochemistry 12, 3055–3063]. The molecular weights of restriction fragments were determined relative to the standard migration patterns of bacteriophage lambda DNA digested with enzyme HindIII [Murray, K. and Murray, N. E. 1975. "Phage lambda receptor chromosomes for DNA fragments made with restriction endonuclease III of *Haemophilus influenzae* and restriction enconuclease I of *Escherichia coli*." J. Mol. Biol. 98, 551–564] or EcoRI [Helling, R. B., Goodman, H. M. and Boyer, H. W. 1974. Analysis of endonuclease R.EcoRI fragments of DNA from lambdoid bacteriophages and other viruses by agarose-gel electrophoresis. J. Virology 14, 1235–1244].

Cointegrate plasmids pUC1019 and pUC1020, and restructured plasmid pUC1024, can be isolated from their *E. coli* hosts by well known procedures, e.g., using the cleared lysate-isopycnic density gradient procedures described above. Once transformants containing pUC1019, pUC1020, or pUC1024 are identified, they are separated as pure entities in a pure culture. These plasmids can be differentiated as distinct entities by their unique restriction patterns as would be predicted by their restriction maps.

As shown herein, plasmid pUC1019 can be used as a substrate for in vitro deletion restructuring, e.g., pUC1019 can be digested with PvuII to form a derivative lacking some of the PvuII restriction sites. This advantageously also gives a smaller plasmid.

Examples of other vectors which can be used in the invention as a substitute for pBR322 are pBR313, which codes for ampicillin and tetracycline resistance, pSC101, which codes for tetracycline resistance, pCR11, which codes for kanamycin resistance, λ bacteriophage vectors, for example, charon phages, and yeast 2μ plasmid DNA.

Examples of other hosts for the vectors are any *E. coli* K-12 derivative [Bacteriological Reviews, December 1972, pages 525–557] (these have been approved by the NIH Guidelines) and yeasts, other fungi, or other bacteria. It is recognized that these latter hosts would also have to be approved by the NIH Guidelines.

The work described herein was all done in conformity with physical and biological containment requirements specified in the NIH Guidelines.

We claim:

1. *E. coli* CSH50 (pUC1019) having the deposit accession number NRRL B-12252.

2. *E. coli* CSH50 (pUC1020) having the deposit accession number NRRL B-12253.

Figure 2:
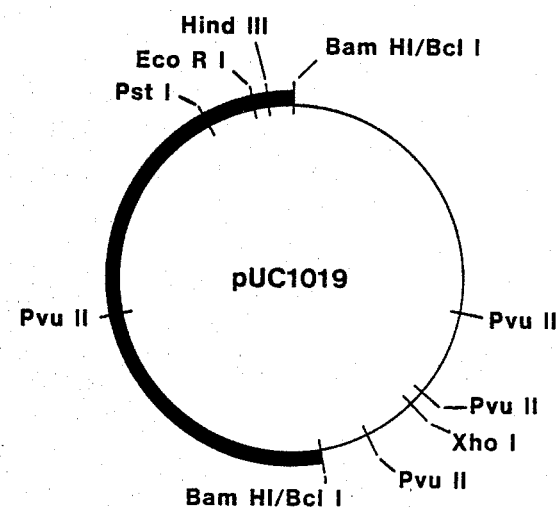

3. Cointegrate plasmid pUC1019, characterized as shown by the restriction map in FIG. 2 of the drawings.

Figure 3:
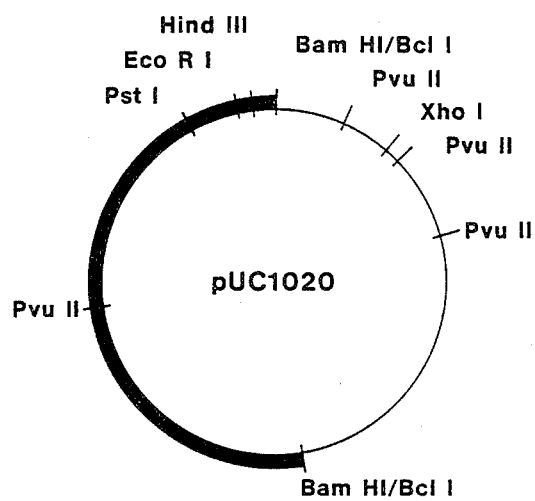
Figure 4:
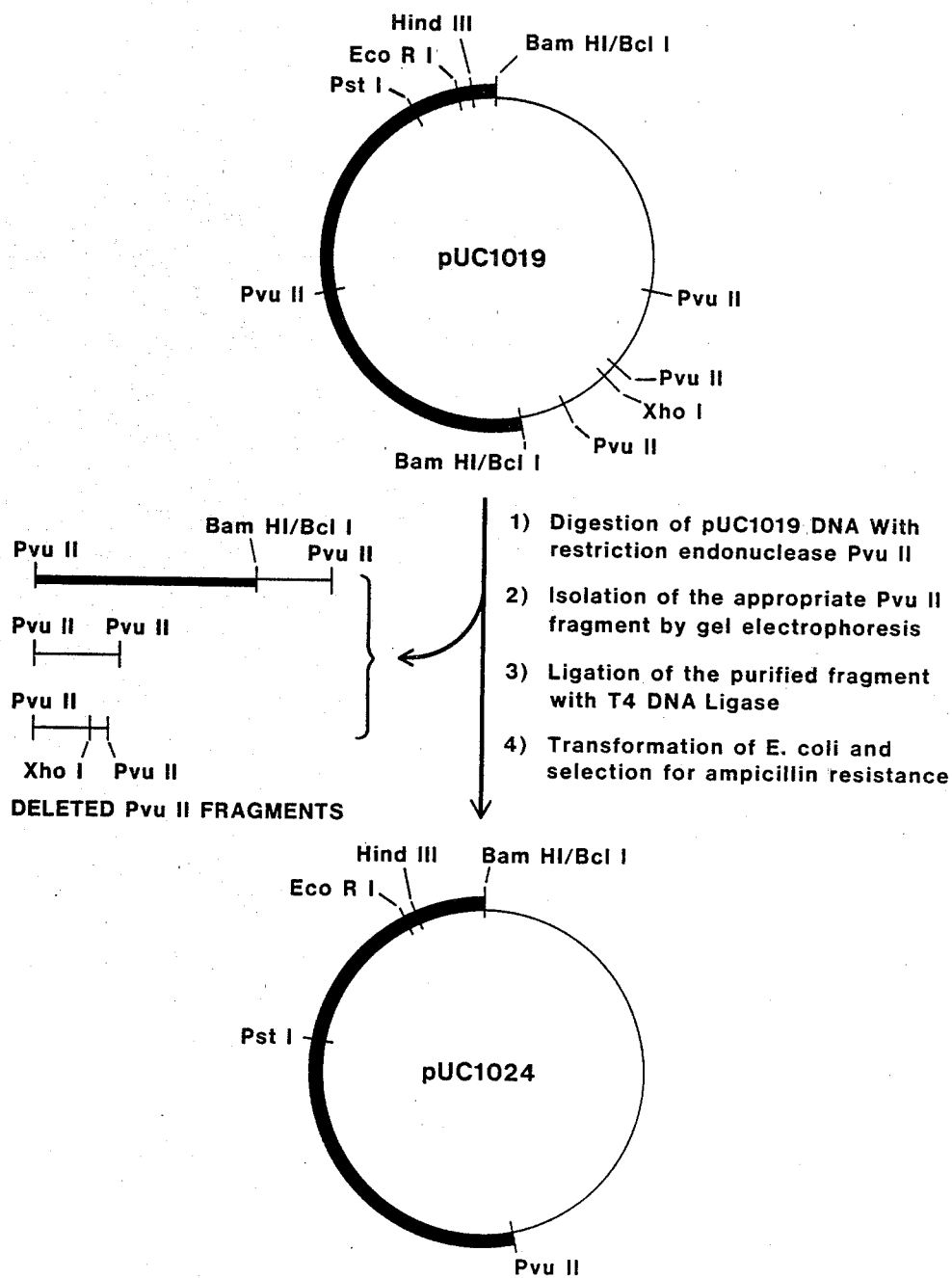

4. Cointegrate plasmid pUC1020 characterized as shown by the restriction map in FIG. 3 of the drawings.

5. A process for preparing cointegrate plasmids pUC1019 and pUC1020 which comprises:
    (a) linearizing plasmid pBR322 by BamHI endonuclease to obtain linear plasmid DNA;
    (b) linearizing plasmid pUC6 by BclI endonuclease to obtain linear plasmid DNA; and
    (c) ligating said linear plasmid DNA from pBR322 and pUC6 to obtain cointegrate plasmids pUC1019 and pUC1020.

6. A process for cloning ca. 4.2 kb BclI restriction endonuclease fragment of plasmid pUC6 into a suitable host which comprises:
    (a) linearizing plasmid pBR322 by BamHI enconuclease to obtain linear plasmid DNA;
    (b) linearizing plasmid pUC6 by BclI endonuclease to obtain linear plasmid DNA;
    (c) ligating said linear plasmid DNA from pBR322 and pUC6 to obtain cointegrate plasmids pUC1019 and pUC1020; and,
    (d) transforming said cointegrate plasmids into said suitable host.

7. A process, according to claim 6, wherein said suitable host is a bacterium.

8. A process, according to claim 7, wherein said bacterium is *E. coli* CSH50.

9. *E. coli* RR1 (pUC1024) having the deposit accession number NRRL B-12254.

Figure 5:
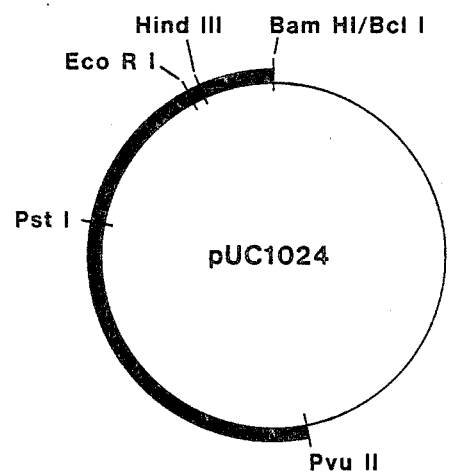

10. Plasmid pUC1024, characterized as shown by the restriction map in FIG. 5 of the drawings.

11. A process for preparing plasmid pUC1024 which comprises:
    (a) digestion of pUC1019 DNA with restriction endonuclease PvuII to obtain fragmented linear plasmid DNA; and,
    (b) ligating the PvuII fragment of said plasma DNA to obtain plasmid pUC1024.

12. A process for cloning plasmid pUC1024 into a suitable host which comprises:
    (a) digestion of pUC1019 DNA with restriction endonuclease PvuII to obtain fragmented linear plasmid DNA;
    (b) ligating the PvuII fragment of said plasmid DNA to obtain plasmid pUC1024; and,
    (c) transforming said plasmid into said suitable host.

13. A process, according to claim 12, wherein said suitable host is a bacterium.

14. A process, according to claim 13, wherein said bacterium is *E. coli* RR1.

* * * * *